US009345633B2

(12) United States Patent
Fuhr et al.

(10) Patent No.: US 9,345,633 B2
(45) Date of Patent: May 24, 2016

(54) CHIROPRACTIC ADJUSTOR SYSTEM AND METHOD

(71) Applicant: ACTIVATOR METHODS INTERNATIONAL, LTD., Phoenix, AZ (US)

(72) Inventors: Arlan W. Fuhr, Phoenix, AZ (US); Michael Liebschner, Pearland, TX (US)

(73) Assignee: Activator Methods International, Ltd., Phoenix, AZ (US)

( * ) Notice: Subject to any disclaimer, the term of this patent is extended or adjusted under 35 U.S.C. 154(b) by 475 days.

(21) Appl. No.: 13/946,788

(22) Filed: Jul. 19, 2013

(65) Prior Publication Data

US 2014/0031866 A1 Jan. 30, 2014

Related U.S. Application Data

(60) Provisional application No. 61/673,711, filed on Jul. 19, 2012, provisional application No. 61/681,398, filed on Aug. 9, 2012.

(51) Int. Cl.

| | |
|---|---|
| ***A61N 5/067*** | (2006.01) |
| ***A61H 1/00*** | (2006.01) |
| *A61H 23/00* | (2006.01) |

(52) U.S. Cl.

CPC .......... *A61H 1/008* (2013.01); *A61H 2023/002* (2013.01); *A61H 2201/0153* (2013.01); *A61H 2201/1207* (2013.01); *A61H 2201/1664* (2013.01); *A61H 2201/5035* (2013.01); *A61H 2201/5061* (2013.01); *A61H 2201/5084* (2013.01); *A61H 2205/081* (2013.01)

(58) Field of Classification Search

CPC ......... A61H 1/00; A61H 1/006; A61H 1/008; A61H 1/0292; A61H 2201/0157; A61H 2201/0153; A61H 2201/1207; A61H 2201/123; A61H 2201/1664; A61H 2201/5035; A61H 2201/5061; A61H 2201/5084; A61H 2205/081; A61H 2023/002

USPC ............... 601/97, 101–111, 78; 606/237–239

See application file for complete search history.

(56) References Cited

U.S. PATENT DOCUMENTS

| | | |
|---|---|---|
| 4,549,535 A | 10/1985 | Wing |
| D323,034 S | 1/1992 | Reinstein |
| D329,291 S | 9/1992 | Wollman |

(Continued)

FOREIGN PATENT DOCUMENTS

| | | |
|---|---|---|
| WO | 2014015301 | 1/2014 |

OTHER PUBLICATIONS

Fuhr, Arlan W.; U.S. Provisional Patent Application entitled: Chiropractic Adjusting Instrument System and Method having U.S. Appl. No. 62/219,303, filed Sep. 17, 2015, 46 pgs.

(Continued)

*Primary Examiner* — Steven Douglas

(74) *Attorney, Agent, or Firm* — Taylor English Duma LLP

(57) ABSTRACT

A portable battery power operated chiropractic adjusting instrument, manipulator or thruster for applying a selectable adjustment energy impulse to a patient through a plunger having a resilient or cushioned head with the energy impulse applied to the plunger being supplied by a solenoid. The adjusting instrument can have annunciators or indicators for preload, readiness to operate, level of energy impulse and the like. The power source can be an internal rechargeable battery or removable rechargeable battery pack.

33 Claims, 13 Drawing Sheets

(56) References Cited

U.S. PATENT DOCUMENTS

| | | | |
|---|---|---|---|
| 5,315,097 | A | 5/1994 | Collins et al. |
| D352,704 | S | 11/1994 | Etoh |
| D352,935 | S | 11/1994 | Etoh |
| D400,258 | S | 10/1998 | Bolleter |
| D406,126 | S | 2/1999 | Massieu et al. |
| D456,809 | S | 5/2002 | Schlieffers |
| 6,572,637 | B1 | 6/2003 | Yamazaki et al. |
| D481,963 | S | 11/2003 | Onuma et al. |
| D526,320 | S | 8/2006 | Brandon et al. |
| 7,097,364 | B2 | 8/2006 | Wang |
| D545,439 | S | 6/2007 | Draudt et al. |
| D585,993 | S | 2/2009 | Kousuge |
| D606,947 | S | 12/2009 | Caprio et al. |
| D609,361 | S | 2/2010 | McGarry et al. |
| D615,430 | S | 5/2010 | Wieberdink et al. |
| D633,625 | S | 3/2011 | Maderazzo |
| D653,761 | S | 2/2012 | Lytle |
| D667,557 | S | 9/2012 | Boudier |
| D670,389 | S | 11/2012 | Chen |
| D681,487 | S | 5/2013 | Lee et al. |
| D695,903 | S | 12/2013 | Tamsiran |
| D703,337 | S | 4/2014 | Fuhr et al. |
| D706,433 | S | 6/2014 | Fuhr et al. |
| 2003/0141370 | A1 | 7/2003 | Hamilton et al. |
| 2003/0195443 | A1 | 10/2003 | Miller |
| 2004/0049137 | A1 | 3/2004 | Tucek et al. |
| 2006/0030908 | A1 | 2/2006 | Powell et al. |
| 2007/0032847 | A1 | 2/2007 | Weckwerth et al. |
| 2007/0150004 | A1 | 6/2007 | Colloca et al. |
| 2009/0270915 | A1 | 10/2009 | Tsai |
| 2010/0137907 | A1 | 6/2010 | Tsai |
| 2013/0030506 | A1 | 1/2013 | Bartolone et al. |

OTHER PUBLICATIONS

Fuhr, Arlan W.; Provisional Patent Application entitled: Chiropractic Adjustor System and Method having U.S. Appl. No. 61/673,711, filed Jul. 19, 2012, 26 pgs.

Fuhr, Arlan W. Provisional Patent Application entitled: Chiropractic Adjustor System and Method having U.S. Appl. No. 61/681,398, filed Aug. 9, 2012, 26 pgs.

Brothers, David B.; International Preliminary Report on Patentability for serial No. PCT/US2013/051373, filed Jul. 19, 2013, mailed Jan. 30, 2015, 9 pgs.

Brothers, David B.; PCT Application entitled: Chiropractic Adjusting Instrument System and Method, having serial No. PCT/US2013/051373, filed Jul. 19, 2013, 41 pgs.

Fuhr, Arlan W.; Issue Notification for U.S. Appl. No. 29/414,407, filed Feb. 28, 2012, mailed Apr. 2, 2014, 1 pg.

Fuhr, Arlan W.; Issue Notification for U.S. Appl. No. 29/414,408, filed Feb. 28, 2012, mailed May 14, 2014, 1 pg.

Fuhr, Arlan W.; Notice of Allowance for U.S. Appl. No. 29/414,407, filed Feb. 28, 2012, mailed Jan. 14, 2014, 10 pgs.

Fuhr, Arlan W.; Notice of Allowance for U.S. Appl. No. 29/414,408, filed Feb. 28, 2012, mailed Jan. 15, 2014, 10 pgs.

Fuhr, Arlan W.; U.S. Design Application entitled: Medical Device, having U.S. Appl. No. 29/414,407, filed Feb. 28, 2012,5 pgs.

Fuhr, Arlan W.; U.S. Design Application entitled: Medical Device, having U.S. Appl. No. 29/414,408, filed Feb. 28, 2012. 5 pgs.

Vicks, Forehead Thermometer, Jul. 11, 2009, amazon.com http://amzn.com/B002KE5X88.

International Search Report and the Written Opinion of the International Search Authority for Application No. PCT/US2013/051373 (mailed Oct. 31, 2013).

CHIROPRACTIC ADJUSTOR SYSTEM AND METHOD

FIELD OF THE INVENTION

The present invention relates generally to a portable chiropractic instrument for use in chiropractic adjustment of musculoskeletal structures. More particularly, the invention relates to a power operated chiropractic adjusting instrument system and method for using same in spinal manipulative therapy to apply desired impact forces or thrusts to a human body.

BACKGROUND OF THE INVENTION

The chiropractic art is generally concerned with adjusting misaligned body structures by manually manipulating the various joints in the human body. Of more specific interest in the art, however, is the spinal column which is comprised of a plurality of interconnected musculoskeletal structures or vertebrae. The human spine is susceptible to many different pathologic abnormalities including misalignment, miscellaneous trauma and pain, and degeneration as a result of age or disease. By employing various chiropractic physical therapy techniques, though, a chiropractor, or one skilled in the chiropractic art, may be able to successfully treat a physiologically abnormal spine. Such treatment often results in immediate relief of pain or discomfort that the patient might be suffering and can improve the overall quality of life of that patient.

Conventional spinal-adjustment techniques can involve the selective application of thrusts or forces to the afflicted and targeted region of the spine. Such conventional spinal-adjustment techniques can include “mobilizing” the spine (i.e., passively moving the spine with relatively slow cyclic or oscillatory motion), or “manipulating” the spine (i.e., applying an impulsive thrust or force in a well-defined direction to a specific region of the spine). Depending on professional affiliations, these techniques are referred to as chiropractic adjustment, osteopathic manipulation, orthopedic manual therapy, and/or spinal manipulative therapy. It is appreciated that such mechanical shockwave therapy is widely used in chiropractic practice.

It is known in the art that a shockwave differs from an acoustic wave in that an acoustic wave generally consists of periodic oscillation whereas a shockwave is a single pulse. In operation, the shockwave applied in a chiropractic context is a mechanical pressure pulse that expands as a half-sine wave within the human body. Further, the applied shockwave’s propagation capabilities and tissue penetration depth depends on the energy of the shockwave and on the tissue damping effect. Viscoelastic damping of the shockwave is minimized at or around the natural frequency of the tissue. It is contemplated that high transmissibility can be achieved at tissue resonance while concurrently reducing the energy requirement of the shockwave generator and diminishing side effects caused by the overstimulation of surrounding tissue.

There are several well-known procedures or techniques for “manipulating” or administering impulsive thrusts to a spine. One technique involves applying one or more thumb thrusts to misaligned or afflicted vertebrae. The ideal force/time wave form for an individual thumb thrust approximates a half-sine wave. As one will appreciate however, thumb thrusts initiated by a human tend to be both imprecise in magnitude and location and tiresome to administer. Another technique involves using a manually operated chiropractic-adjusting instrument. For instance, U.S. Pat. No. 4,116,235, issued to Fuhr et al., U.S. Pat. No. 6,702,836; issued to Fuhr et al., U.S. Pat. No. 6,379,375, issued to Fuhr et al., U.S. Pat. No. 5,626,615; issued to Keller et al., U.S. Pat. No. 5,656,017; issued to Keller et al., and U.S. Pat. No. 4,498,464, issued to Morgan, Jr., disclose such instruments.

Instrumented spinal manipulation, such as via the presently disclosed device has substantially overtaken the field of spinal manipulative therapy. Conventionally, these high velocity, low amplitude (HVLA) mechanical shockwave therapy devices are placed at the anatomic site of interest and triggered to deliver a force-time profile lower in amplitude, shorter in duration and with a faster force rate compared with a manually applied manipulation techniques. Throughout the years it has also been known that power driven mechanical shockwave therapy devices at times can offer benefits or advantages in use over the manually operated devices. Particularly, there is a current need for a compact, lightweight device that is portable and yet can be easily and repetitively apply a consistent desired impulse onto the patient at a desired location and direction without strength or fatigue issues compromising the treatment.

Electric solenoid operated adjusting instrument s such as ones described in U.S. Pat. No. 4,841,955 issued to Evans, U.S. Pat. No. 4,682,490, issued to Adelman, U.S. Pat. No. 7,144,417 issued to Colloca, et al., or U.S. Pat. No. 8,083,699 issued to Colloca, et al. can provide adjusting and controllability benefits over manual devices. However, to date such electric solenoid operated adjusting instrument s have not been able to adequately reproduce the desired half sine wave form impulse.

SUMMARY

The present chiropractic adjusting instrument system and method is capable of imparting desired energy impulses thereon a patient in the conduct of spinal manipulative therapy. To accomplish this, the invention provides a chiropractic adjusting instrument system and method that is configured to selectively apply desired impact forces or thrusts to a human body that can closely approximate the ideal half sine wave impulse configuration.

In one aspect, a portable chiropractic adjusting instrument, manipulator or thruster is provided that has an axially movable plunger having a resilient or cushioned thrust nose piece that is mounted to a distal end of the plunger. In one aspect, a proximal end portion of the plunger can be selectively placed into operative contact with a distal end of a selectively axially movable core of a solenoid so that energy exerted by the distal end of the core on the proximal end portion of the plunger can effect the application of a selectable adjustment energy impulse to a patient. In various aspects, it is contemplated that the chiropractic adjusting instrument system can be configured to be “tunable” or settable as to load, amplitude, and frequency within a user selected range of natural frequency.

In a further aspect, the chiropractic adjusting instrument can have annunciators or indicators for preload, readiness to operate, level of energy impulse and the like.

In a further aspect, the chiropractic adjusting instrument can have a self contained power source which is long lasting and yet can be rechargeable or replaceable. It is contemplated that the power source can be an internal rechargeable battery or removable rechargeable battery pack. Optionally, the power source could be a conventional AC or DC power supply source.

Additional embodiments of the invention will be set forth, in part, in the detailed description, figures, and claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

These and other features of the preferred embodiments of the invention will become more apparent in the detailed description in which reference is made to the appended drawings wherein.

DETAILED DESCRIPTION

Figure 1:
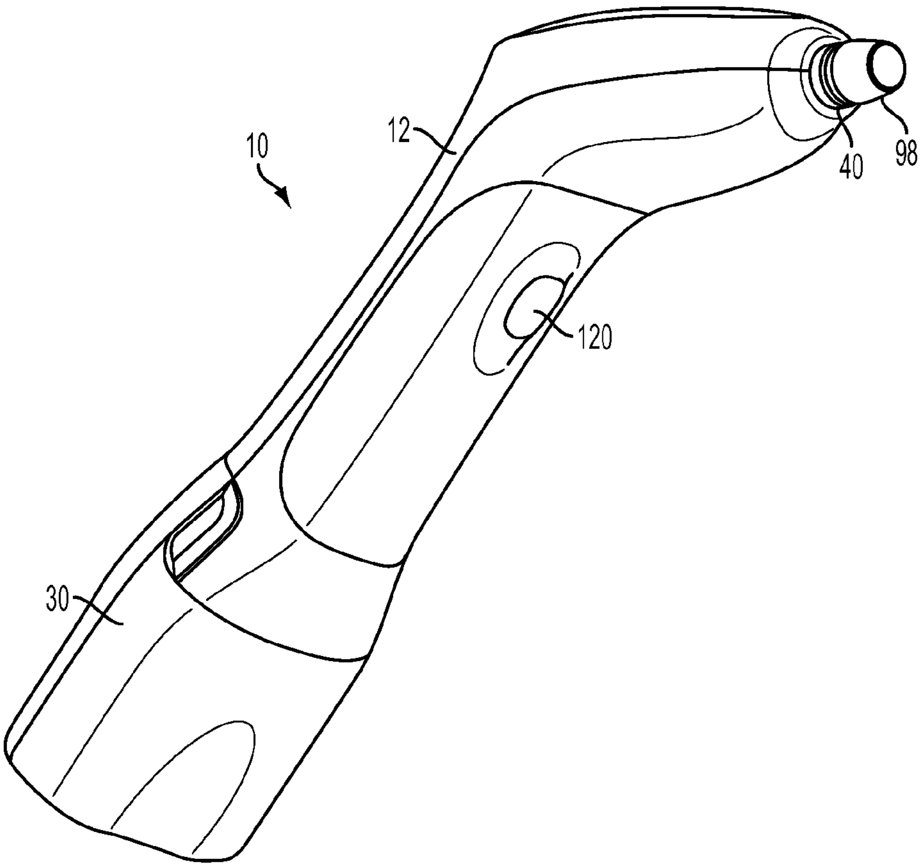
FIG. 1 is a perspective front side view of a chiropractic adjusting instrument.
Figure 2:
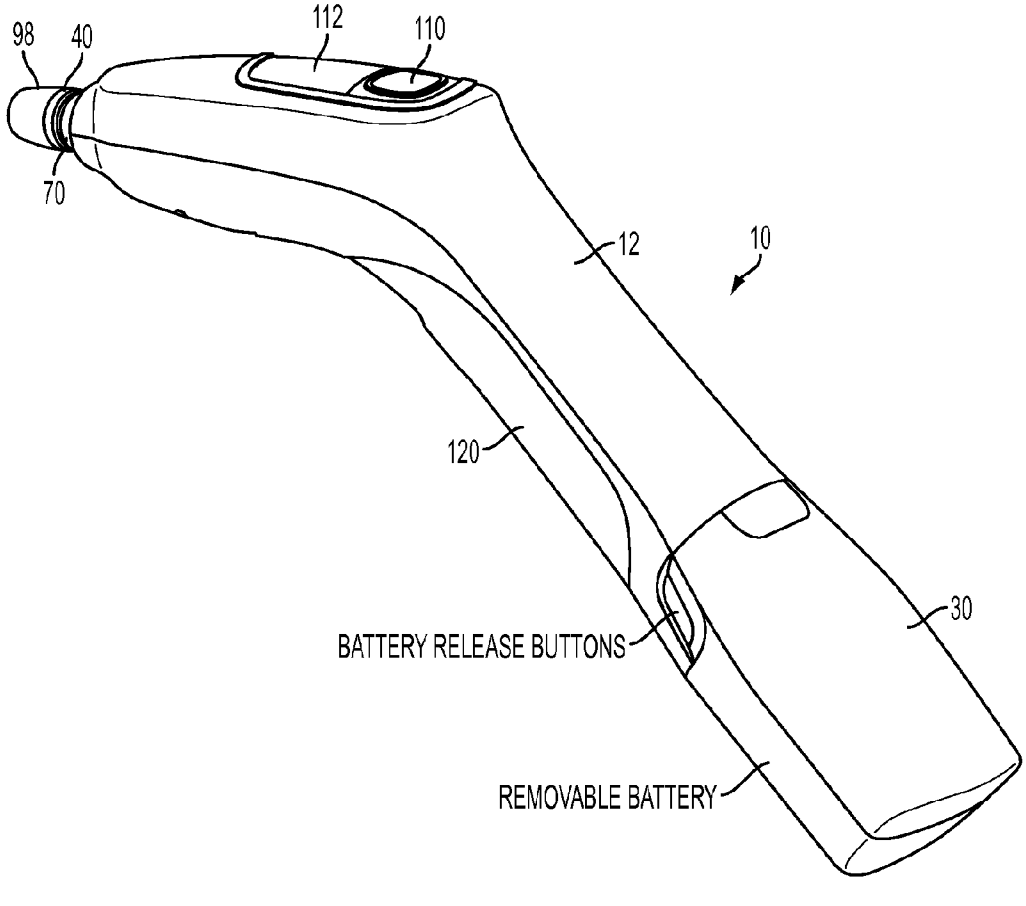
FIG. 2 is a perspective rear side view of a chiropractic adjusting instrument.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to an "impulse setting" can include two or more such impulse settings unless the context indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

The present invention may be understood more readily by reference to the following detailed description of preferred embodiments of the invention and the examples included therein and to the Figures and their previous and following description.

The present chiropractic adjusting instrument system and method is capable of imparting desired energy impulses thereon a patient in the conduct of spinal manipulative therapy. To accomplish this, the invention provides a chiropractic adjusting instrument system and method that is configured to selectively apply desired impact forces or thrusts to a human body that can closely approximate the ideal half sine wave impulse configuration.

In one aspect, and referring now to FIGS. 1-6, a portable chiropractic adjusting instrument, manipulator or thruster 10 is provided that has an energy application assembly 20 that is mounted therein a housing 12. In one aspect, it is contemplated that the housing 12 can have an external shape that ergonomically allows for single handed grasping and operation of the chiropractic adjusting instrument. As shown, one contemplated shape of the housing is a gun shape. In one aspect, it is contemplated that the housing 12 can be formed from a non-conductive material such as, for example and without limitation, a polymer.

In a further aspect, the chiropractic adjusting instrument 10 can have a self contained power source 30. In various aspects, it is contemplated that the self contained power source can be long lasting and can be rechargeable and/or replaceable. For example and without limitation, the power source 30 can be an internal rechargeable battery or a removable rechargeable battery pack. Optionally and not shown, it is contemplated that the housing can include a power cord that is configured to be conventionally coupled to an external conventional AC or DC power supply source.

In a further aspect, the housing 12 of the chiropractic adjusting instrument 10 can define a port 14 at one end of the housing and an interior cavity 16 for mounting an electromechanical drive assembly 35. In various aspects, the electromechanical drive assembly 35 can comprise a thrust tip subassembly 40 that is selectively coupled to a solenoid sub assembly 80.

Figure 4:
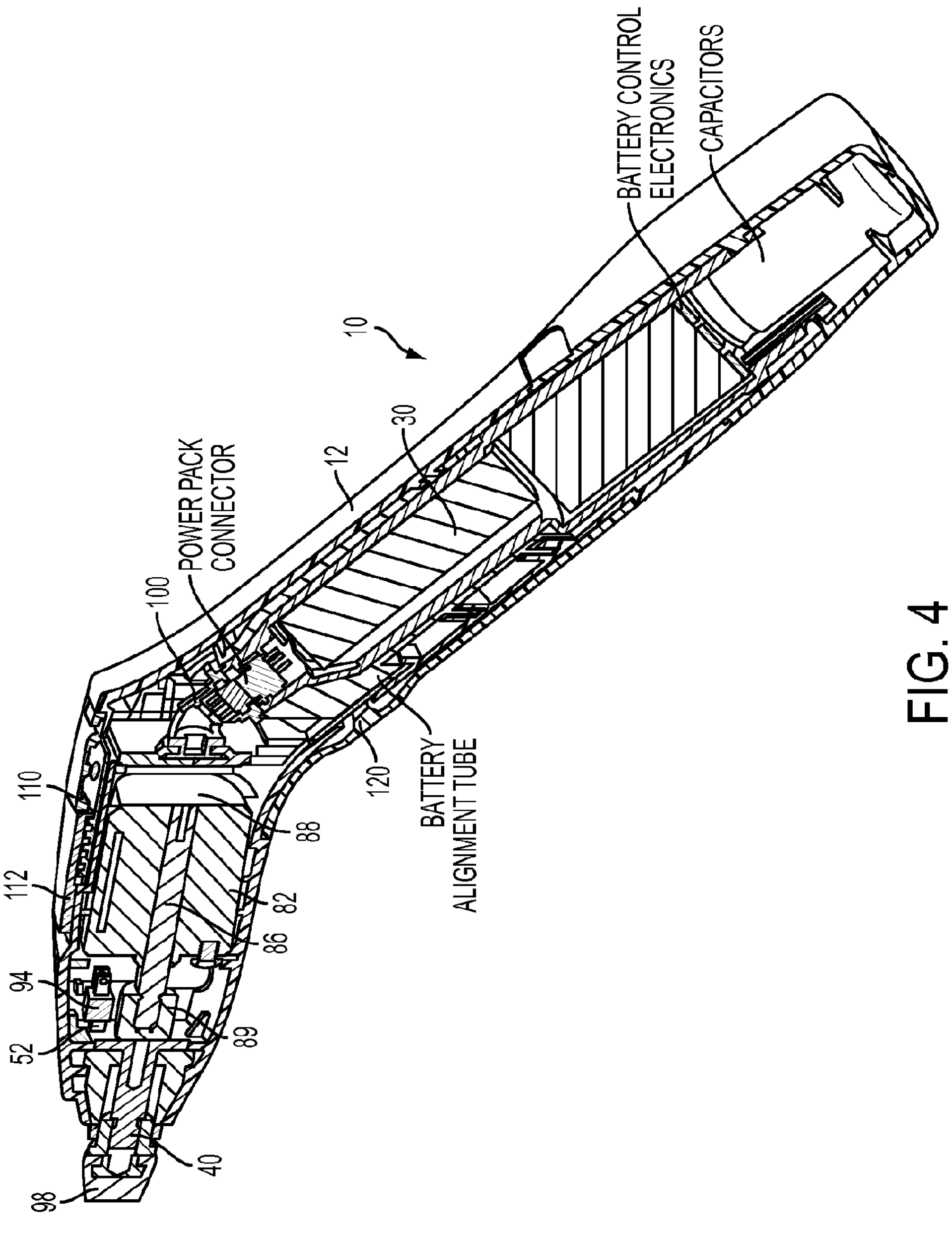
FIG. 4 is a perspective cross-sectional view of the chiropractic adjusting instrument of FIG. 1, showing an electromechanical drive assembly 50 mounted therein a housing of the chiropractic adjusting instrument.
Figure 5:
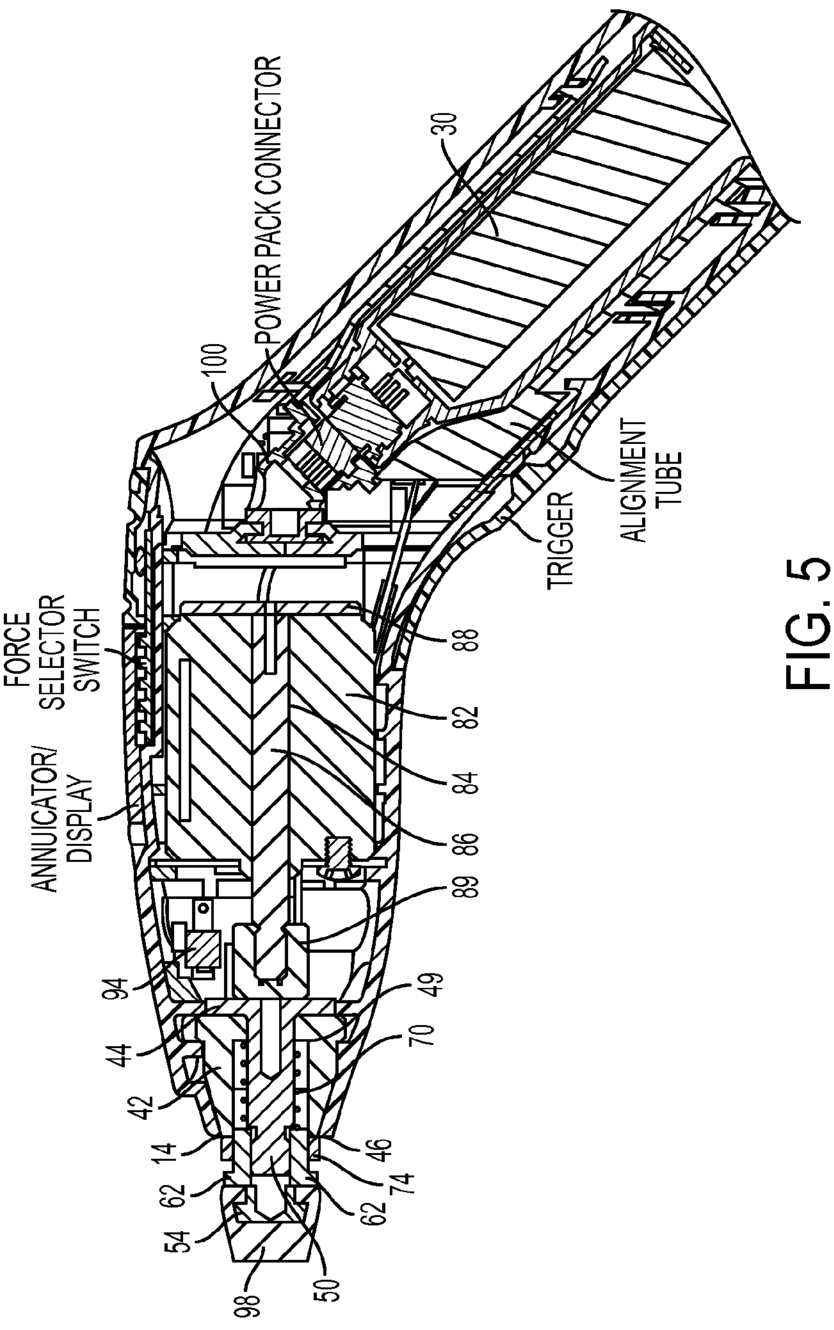
FIG. 5 is partial cross-sectional view of the chiropractic adjusting instrument of FIG. 1.
Figure 6:
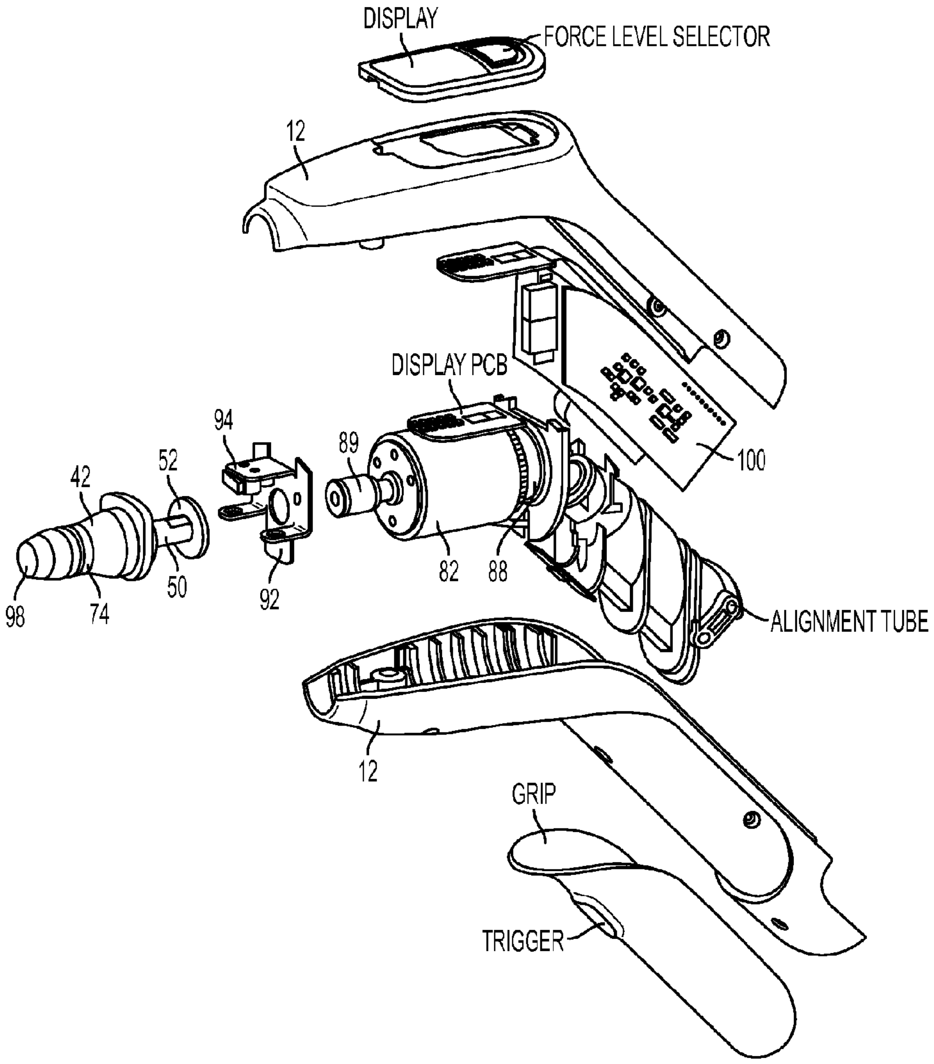
FIG. 6 is a perspective side exploded view of chiropractic adjusting instrument of FIG. 1.

In one aspect, the thrust tip subassembly 40 can comprise a thrust tip mount 42, a thrust tip plunger 50, at least one bias element 70, and a resilient and/or cushioned noise piece 98. In one aspect, the thrust tip mount 42 has a substantially planar first end 44 and a spaced substantially planer second end 46. A core 48 is defined that extends along an elongate longitudinal axis of the thrust tip mount 42. In a further aspect, the core 48 has a first internal diameter proximate the first end of the thrust tip mount and a second, expanded internal diameter extending a predetermined distance from the second end toward the first end. As one will appreciate, a step 49 is defined at the transition in the core 48 from the first internal diameter to the enlarged second internal diameter. As shown in FIGS. 4 and 5, the thrust tip mount 42 can be positioned in the housing such that the second end 46 of the thrust tip mount 42 extends to the port 14 of the housing 12. In another aspect, it is contemplated that the second end 46 of the thrust tip mount can be positioned substantially co-planer to the walls of the housing 12 that define the port 14.

In another aspect, the thrust tip plunger 50 can comprise a substantially planar base plate 52, an elongate rod 54 and a tip 56. As shown in the figures, a proximal end of the elongate rod 54 is connected to and extends substantially transverse to the base plate 52. In one aspect, the rod 54 can have a cylindrical shape and have an outside diameter that is configured to be slideably received within the portion of the defined core 48 of the thrust tip mount 42 that is sized to the first internal diameter. In another aspect, the tip 56 of the thrust tip plunger 50 can have an end surface 58 that defines an internal cavity that is conventionally configured for the fixed coupling of the distal end of the rod 54. The external surface 60 of the tip proximate the end surface has a first outside diameter and has a shape that is configured to be slideably received therein the portion of the defined core 48 of the thrust tip mount 42 that is sized to the second internal diameter. In another aspect, at a predetermined distance from the end surface 58 of the tip 56, the external surface 60 of the tip defines a shoulder stop 62 as the external surface expands to an enlarged diameter.

As one skilled in the art will appreciate, when assembled, the thrust tip plunger 50 is axially movable relative to the fixed thrust tip mount 42 about a between an extended position and a preload compressed position. In the extended position, the tip 56 of the thrust tip plunger 50 is positioned a maximal axial distance from the first end 44 of the trust tip mount, the base plate 52 is in contact with first end 44 of the thrust tip mount 42 to constrain any further axial movement of the thrust tip plunger 50 in an actuation direction (which is coaxial to the longitudinal axis of the thrust tip mount 42), the end surface 58 of the tip 56 and a portion of the external surface 60 of the tip proximate the end surface are positioned therein the portion of the defined core 48 of the thrust tip mount 42 that is sized to the second internal diameter such that the end surface 58 is spaced at a maximal axial distance from the step 49 of the thrust tip mount 42, and the shoulder stop 62 of the tip 56 is positioned a maximal axial distance from the second end of the thrust tip mount 42. In the preload compressed position, the tip 56 of the thrust tip plunger is positioned at a reduced axial distance from the first end 44 of the trust tip mount, the base plate 52 is spaced at a predetermined distance from the first end of the thrust tip mount 42, the end surface of the tip 56 is spaced at a minimal axial distance from the step 49 of the thrust tip mount 42, and the shoulder stop 62 of the tip 56 is positioned a minimal axial distance from the second end of the thrust tip mount 42.

As shown in the figures, the portion of the core 48 having the expanded second internal diameter, a portion of the external surface of the rod 54 and the respective end surface 69 of the tip 56 and step 49 of the trust tip mount 42 define an internal cavity 64 that defines a volume that is maximal in the extended position and minimal when in the preload compressed position. In one aspect, at least one bias element 70 is configured to resiliently urge the movement of the thrust tip plunger 50 to the extended position relative to the thrust tip mount 42. In one aspect, it is contemplated that the at least one bias element 70 can comprise a spring 72 that is positioned therein the internal cavity 64 and is interposed there between the respective end surface 69 of the tip 56 and step 49 of the trust tip mount 42. In various aspects, the spring 72 can be formed from a material that exhibits a desired spring force, such as, for example and without limitation, metals (e.g., steel), polymers, and the like. In a further aspect, it is contemplated that the at least one bias element 70 can further comprise a conditioning ring 74 that is positioned thereon the external surface 60 of the tip 56 there between the respective shoulder stop 62 of the tip and the surface of the second end of the thrust tip mount 42. In various aspects, the conditioning ring 74 can be formed from a material that exhibits a desired spring force, such as, for example and without limitation, compressible polymers, and the like.

In operation and as shown in FIGS. 7-10, when the thrust tip plunger 50 is moved to the compressed position, the spring 70 is maximally compressed there between the respective end surface 69 of the tip 56 and step 49 of the trust tip mount 42 and, if used, the conditioning ring 74 is maximally compressed there between the respective shoulder stop 62 of the tip and the surface of the second end of the thrust tip mount 42. As one skilled in the art will appreciate, the spring force provided by the at least on bias element 70 is a constant based upon the construct of the at least one bias element and the distance that the at least one bias element is compressed to reach the fixed compressed position.

Figure 3:
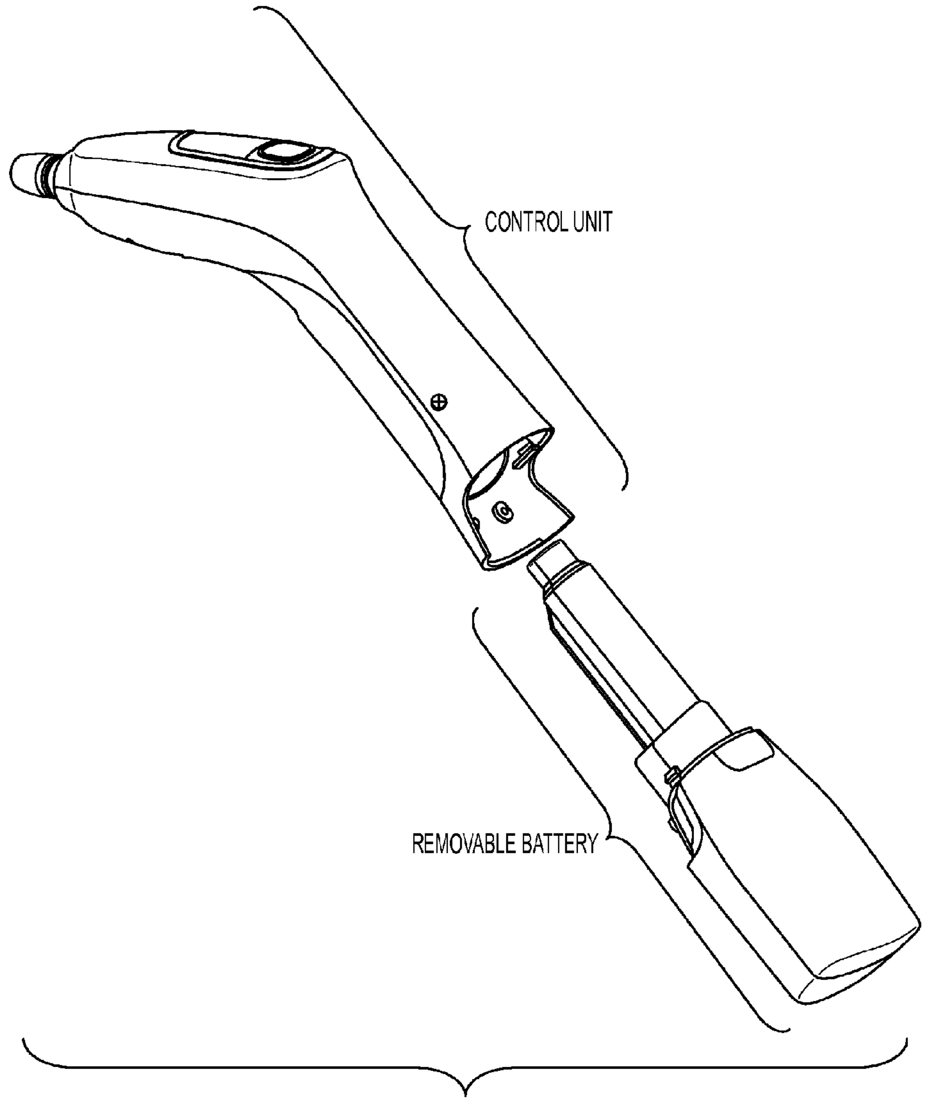
FIG. 3 is a perspective read side view of the chiropractic adjusting instrument of FIG. 1, showing a rechargeable power source disconnected from a portion of a housing of the chiropractic adjusting instrument.

In a further aspect, the solenoid subassembly 80 can comprise a conventional solenoid 82 that defines a core 84 and that has a solenoid rod 86 that is selectively and conventionally biaxially movable therein the core 84 along a longitudinal axis of the solenoid in response to selective application or energization by a current supplied by the power source. In one aspect, it is contemplated that the longitudinal axis of the solenoid 82 is co-axial to the longitudinal axis of the thrust tip mount (collectively the "operational axis") and the actuation direction of the chiropractic adjusting instrument. As shown, the solenoid 82 is mounted inside the housing 12 in a stationary position such that the solenoid rod 86 is selectively axially movable along the longitudinal axis and along the actuation direction. In another aspect, the solenoid subassembly 80 can also comprise a back plate 88 that is connected to the proximal end of the solenoid rod 86 and acts to limit the axial movement of the solenoid rod 86 in the actuation direction upon actuation of the solenoid. As shown in FIG. 3, the back plate is in contact with the back portion of the solenoid when the solenoid rod 86 reaches its maximal extended position upon actuation. In one aspect, the solenoid subassembly can further comprise a hammer element 89 that is coupled to the distal end of the solenoid rod 86.

Figure 7:
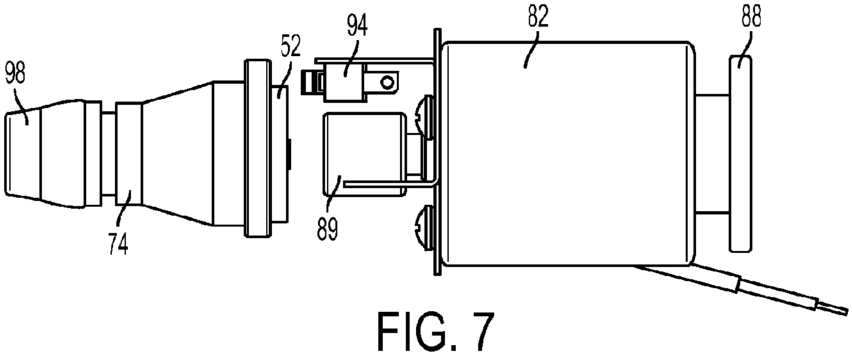
FIG. 7 is a schematic illustration of the electromechanical drive assembly and a preload travel limiter assembly in a rest position. In this example, the preload travel limiter assembly has an optional preload safety switch. Shown is a thrust tip plunger to an extended position and a base plate of the thrust tip plunger is contact with the first end of a thrust tip mount. Further shown is a hammer coupled to a solenoid rod of a solenoid that is spaced a maximal distance from the base plate of the thrust tip plunger.
Figure 8:
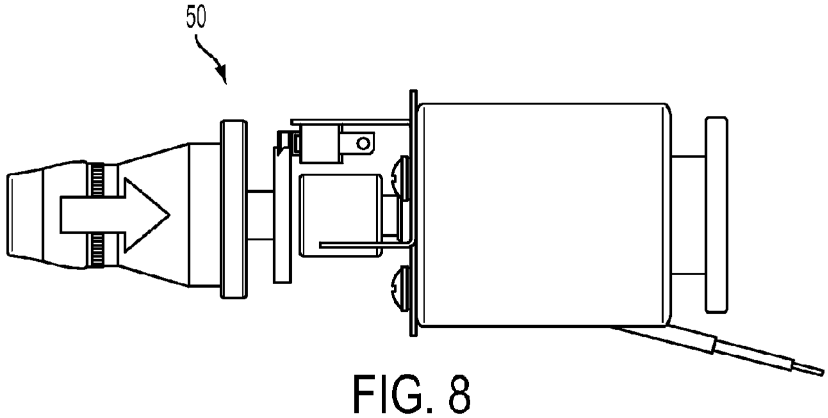
FIG. 8 is a schematic illustration of the electromechanical drive assembly and the preload/safety assembly in a preload compressed position. Shown is a thrust tip plunger moved in a direction opposite to the actuation direction to a preload compressed position, which compresses an at least one bias element to a desired reload compressed level, and a base plate of the thrust tip plunger being in releasable contact with a preload safety switch. Further shown is a hammer coupled to a solenoid rod of a solenoid that is spaced a distance less than the maximal distance from the base plate of the thrust tip plunger.
Figure 9:
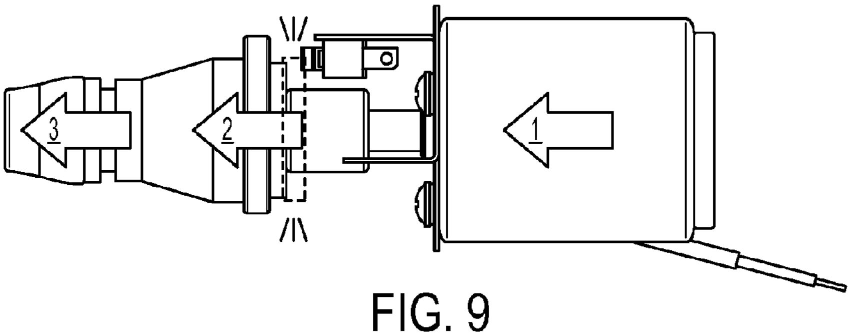
FIG. 9 is a schematic illustration of the electromechanical drive assembly and the preload/safety assembly upon actuation or energization of the solenoid subassembly and the resulting interaction of the solenoid subassembly with the trust tip subassembly, which results in the application of a controlled energy impulse to a patient via the tip portion of the trust tip subassembly. Shown is the solenoid being actuated to force the axial movement of the hammer of the solenoid subassembly into contact with the base plate of the thrust tip plunger to forcibly drive the base plate of the thrust tip plunger into contact with the first end of a thrust tip mount so that the tip portion of the thrust tip plunger is moved in the actuation direction back toward the extended position. Further shown is a base plate of the solenoid subassembly in contact with a back portion of the solenoid to limit the axis movement of the solenoid rod in the actuation direction.
Figure 10:
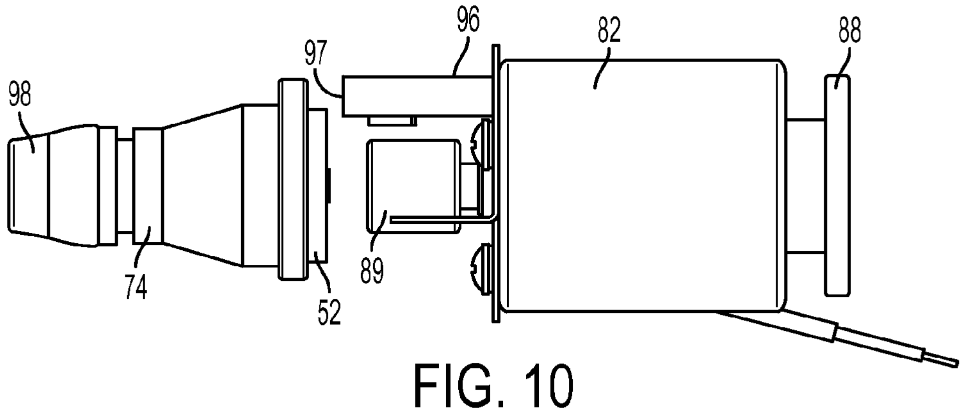
FIG. 10 is a schematic illustration of the electromechanical drive assembly and a preload travel limiter assembly in a rest position. Shown is a mounting plate having an arm that extends outwardly from the surface of the mounting plate substantially in the actuation direction. In this aspect, the arm defines a distal end that is spaced a fixed predetermined distance from the surface of the mounting plate. Further shown is a hammer coupled to a solenoid rod of a solenoid that is spaced a maximal distance from the base plate of the thrust tip plunger. In this aspect, the distal end of the arm can be positioned to interfere with the rearward movement (opposite of the actuation direction) of the thrust tip plunger of the thrust tip assembly, e.g., the distal tip of the arm is configured to act as a stop by interfering with and contacting the base plate of the thrust tip plunger of the thrust tip assembly to limit the maximal rearward travel of the thrust tip plunger.
Figure 11:
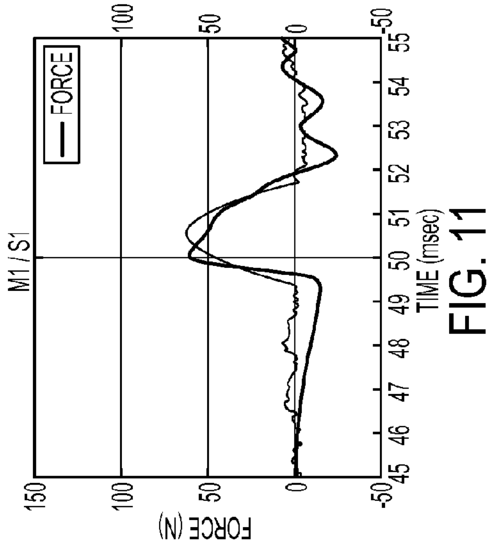
FIGS. 11-14 are graphical illustrations comparing actual energy thrust curves/impulses generated by the chiropractic adjusting instrument of FIG. 1 at various selected actuation levels compared to the idealized half-sine thrust wave forms. In the graphs, the dark line is the actual energy curve and the thinner line is the idealized half sine thrust wave form. As shown in the figures, the actual generated energy curve of the chiropractic adjusting instrument of FIG. 1 approximates a half-sine wave that is smooth, accelerates very fast, then slows down and stops. There is exhibited a smooth transition from an uphill portion of the curve to a complete stop and then to a downhill portion of the curve. It is contemplated that the separation of the hammer element of the solenoid subassembly from the back plate of the thrust tip plunger provides for a plurality of impulses to be applied to the patient upon a single actuation of the chiropractic adjusting instrument of FIG. 1 (the impulse as a result of the stored energy of the at least one bias element and the impulse as a result of the impact and drive of the hammer element upon the base plate of the thrust tip plunger).
Figure 12:
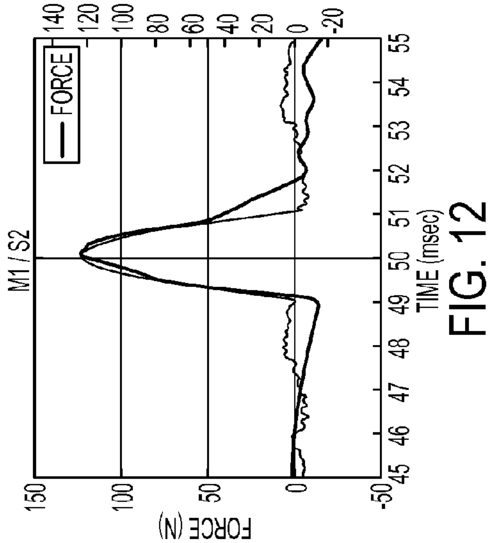
Figure 13:
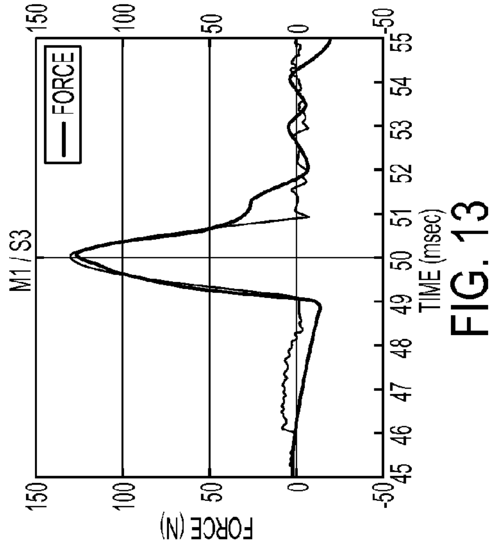
Figure 14:
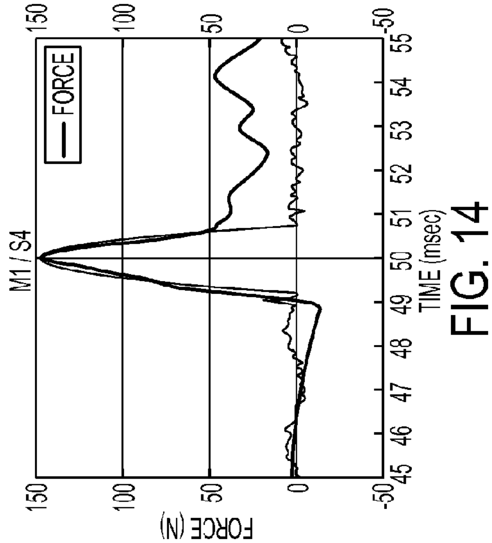

In operation and as shown in FIGS. 7-8 and 10, when the chiropractic adjusting instrument is at rest, the hammer element 89 is spaced from the base plate 52 at a maximal distance. As the thrust tip plunger of the thrust tip assembly is moved axially to the preload compressed position in a direction opposite to the actuation direction, the spacing between the hammer element 89 and the base plate 52 is reduced to a minimal distance. However, it is noteworthy that in the preload compressed position, the hammer element 89 is spaced from the base plate 52 at a predetermined distance and is not in contact with the base plate 52. Only upon actuation of the solenoid subassembly 80, and the subsequent constrained movement of the solenoid rod 86, is the hammer element 89 placed into contact with the base plate 52 to drive the thrust tip plunger of the thrust tip assembly along the actuation direction to the extended position.

As one skilled in the art will appreciate, the force applied by the electromechanical drive assembly 50 is an additive force that comprised the substantially constant force applied by the at least one bias element 70 and the variable and selective force that can be applied to the thrust tip plunger of the thrust tip assembly via the hammer element of the solenoid at a result of the selective application of energy to the solenoid. As shown in FIGS. 11-15, the actual generated energy curve of the chiropractic adjusting instrument approximates closely a half-sine wave that is smooth, accelerates very fast, then slows down and stops. There is exhibited a smooth transition from an uphill portion of the curve to a complete stop and then to a downhill portion of the curve. It is contemplated that the separation of the hammer element of the solenoid subassembly from the back plate of the thrust tip plunger provides for a plurality of impulses to be applied to the patient upon a single actuation of the chiropractic adjusting instrument. It is further contemplated that the additive force is a combination of the impulse that is a result of the stored energy of the at least one bias element and the impulse that is the result of the impact and drive of the hammer element upon the base plate of the thrust tip plunger.

In a further aspect, and referring to FIGS. 7-10, the chiropractic adjusting instrument 10 can comprise a preload travel limiter assembly 90 that can have a mounting plate 92 and, optionally, a preload/safety switch 94. In one aspect the mounting plate can be mounted therein the housing 12 and can be positioned at or adjacent to the solenoid 82. The mounting plate can also have an arm 96 that extends outwardly from the surface of the mounting plate substantially in the actuation direction. In one aspect, the arm 96 can extend substantially parallel to the operational axis. In this aspect, the arm 96 can define a distal end 97 that is spaced a fixed predetermined distance from the surface of the mounting plate. In this aspect, the distal end 97 of the arm can be positioned to interfere with the rearward movement (opposite of the actuation direction) of the thrust tip plunger of the thrust tip assembly, e.g., the distal tip 97 of the arm is configured to act as a stop by interfering with and contacting the base plate of the thrust tip plunger of the thrust tip assembly to limit the maximal rearward travel of the thrust tip plunger. Further, in the described aspect, the distal end 97 of the arm 96 is configured such that hammer element 89 is spaced from the base plate 52 of the thrust tip plunger at a predetermined distance and is not in contact with the base plate 52 when the thrust tip plunger is compressed to the preload compressed position.

Optionally, the preload/safety switch 94 can mounted to a distal portion of the arm 96 and can be configured to selectively releasably couple to the base plate 52 of the thrust tip plunger 50 when the thrust tip plunger is compressed to the preload compressed position. One will appreciate that the preload term refers to the stored mechanical energy provided by the compression of the at least one bias element 70. Further, and as shown in FIG. 8, the preload/safety switch 94 is mounted on the arm 96 such that hammer element 89 is spaced from the base plate 52 at a predetermined distance and is not in contact with the base plate 52 when the thrust tip plunger is compressed to the preload compressed position. Optionally, the mounting plate 92 can be configured to act at a mount for the solenoid and can define an opening that is suitably sized and shaped for the solenoid rod to be able to move axially without impediment.

In yet another aspect, the chiropractic adjusting instrument 10 can comprise a control electronic assembly 100 that is operable connected to the power source 30 to provide current, such as a direct current or an alternating current, to the solenoid 82 to impart impulse energy from the solenoid rod 86 and the coupled hammer element 89 to the thrust tip plunger 50 and hence to the resilient or cushioned noise piece 98 that is coupled to the tip distal most portion of the thrust tip plunger. As one will appreciate, the application of current to the solenoid 82 is controlled by the control electronic assembly 100 so that the applied energy impulse to the patient is reproducible.

In the preferred embodiment of the invention, the control electronic assembly 100 comprises at least a computational control circuit 102 and a non-volatile storage device 104. The computational control circuit 102 can utilize a microprocessor or any other comparable processing device to conduct mathematical processing for adjusting power supplied to the solenoid 82 to achieve the power outputted by the actuated solenoid rod. The non-volatile storage device 104 can use any comparable non-volatile memory format, for example, dynamic random access memory (DRAM), flash memory, magneto-resistive random access memory (MRAM), and the like. As one will appreciate, the non-volatile storage device can provide storage for various computational equations, mathematical constants, power management and solenoid operational software, timers, counters and information regarding various desired impulse types and levels, and the specific operational requirements which are used by the computational control circuit during processing and operation.

In one aspect, the computational control circuit 102 can be configured to diagnose/analyze the voltage and the frequency of the supplied current and can control the on-off duration of the application of the current to the solenoid to thereby energize the solenoid reproducibly so that the energy impulse supplied to the patient via the resilient or cushioned noise piece of the chiropractic actuator can produces a pulse duration or impulse of a desired wave form. More particularly, the energy impulse can substantially conform to the desired half sine wave shape. As further shown in FIGS. 10-13, graphs of actual energy impulses is plotted with a model of the desired high sine wave shape for four varied energy impulses. It is noteworthy that the energy impulses generated by the chiropractic adjusting instrument 10 of the present invention substantially mirror the desired or ideal model half sine wave shapes. In various aspects, the actual energy impulse substantially mirror or conforms to at least 90% of the desired wave shape; preferably to at least 93% of the desired wave shape, and still more preferably to at least 95% of the desired wave shape. It is also noteworthy that the shape confirmation between the actual energy impulse and the desired half sine impulse waveform is especially conforming in the first half of the actual energy impulse.

In an optional aspect, the computational control circuit 102 can be programmed to diagnose the chiropractic adjusting instrument 10 statuses; for example, whether or not the thrust tip plunger is in the preload compressed position and is releasably coupled to the preload/safety switch.

In various aspects, the control electronic assembly 100 can further comprise a level selector switch 110 positioned on the exterior of the housing and having a plurality of selectable positions for controlling the frequency and/or amplitude of the applied energy impulse. In another aspect, the control electronic assembly 100 can also comprise an annunciator or indicator 112 that is coupled to the computational control circuit to provide operator indications, which can exemplarily include, without limitation, power-on indication, preload ready indication, impulse level indication, and error indication. In one example, the indicator 112 can comprise a LED display mounted to the housing 12.

In a further aspect, the computational control circuit 102 can be configured to measure the output of the chiropractic adjusting instrument 10 over a predetermined period or duration of time. In various aspects, means for measuring the output can comprise at least one transducer or a plurality of transducers that are coupled to and configured to measure force and acceleration of the thrust tip plunger 50. In yet another aspect, means for measuring the output can comprise an accelerometer. Such an accelerometer can generate the desired acceleration signal. In this aspect, it is contemplated that the accelerometer can be a conventional accelerometer, such as, for example and without limitation, a piezo type accelerometer, MEMS type accelerometer, and the like.

In one aspect, force and acceleration signals generated by the at least one transducer can be analyzed to determine the impedance of the thrust tip plunger 50 during and immediately after activation. Further, it is contemplated that the force and acceleration signals generated by the at least one transducer can be analyzed to generate other applicable physical parameters. For example and without limitation, the acceleration signal can be time integrated to obtain velocity of the thrust tip plunger 50 and then time integrated again to obtain displacement of the thrust tip plunger 50. For example and without limitation, the ratio of force divided by displacement represents dynamic stiffness of the chiropractic adjusting instrument 10 and the patient. As one skilled in the art will appreciate, other combinations of these force and acceleration signals and resultant parameters can represent different physical means.

In another exemplary aspect, force output can be measured indirectly through the electric power applied to the solenoid. In this aspect, it is contemplated that the applied electric power can be described as the product of the electric current and the applied voltage or the product of the electric current squared times the electric resistance. In this aspect, the electric current can be measured by conventional means, such as, for example and without limitation, a current transducer, a small integrated resistor, and the like. Further, voltage can be measured by conventional means, such as, for example and without limitation, a large resistor, an integrated circuit (e.g., an operational amplifier wired as voltage follower) in parallel to the solenoid, and the like. It is contemplated that the computational control circuit 102 can be configured to correlate the measured electric power or electric current to values representing the solenoid output thrust force.

In one aspect, it is contemplated that the signal analysis can be performed by the computational control circuit 102 of the chiropractic adjusting instrument 10. The results of the signal analysis can be depicted on the indicator 112 as a feedback to the device operator. Optionally, it is contemplated that the results of the signal analysis or the generated signals can be conventionally transferred to an external console (not shown) and then depicted for use by the device operator. One person skilled in the art can optionally elect to depict the data as graphs, charts, figures, percentage, absolute values, and the like.

In one aspect, it is contemplated that the signal analysis and derived results can be used to assess the tissue response of the patient, which can be used to determine treatment need or current state of the health of the patient. In this aspect, a comparative analysis can be made between a pre-defined normal tissue state of the patient and the current measurements that reflect the current tissue state of the patient. Optionally, the comparative analysis can be made with comparison to other reference data, such as, for example and without limitation, the patient's own prior data, a pooled dataset from other patients and healthy individuals, reference charts, and the like. In another aspect, the determined signals, signal analysis, and/or derived results signals can be used to assess the tissue response of the patient before and after therapeutic intervention. It is contemplated that the determined differential measure can be used by one skilled in the art to determine therapeutic success or success of the medical intervention.

In one aspect, the chiropractic adjusting instrument 10 can comprise a triggering system 120 for triggering the electromechanical drive system via the control electronic assembly 100. In one aspect, the triggering system 120 can comprise a trigger and a trigger spring so the operator can selectively cause the control electronic assembly to direct the electromechanical drive assembly 35 to fire. In an optional aspect, the triggering system 120 can also comprise a trigger switch 122 that is activated by the preload/safety switch 94. The trigger switch 122 can be configured to act as an interlock or safety device such that the electromechanical drive assembly 35 can not be actuated unless the preload/safety switch 94 is activated. In various aspects, the trigger switch 122 can be any type of conventional optical, electrical, mechanical or magnetic switch and may be configured in many ways such that it is coupled to the electromechanical drive assembly to prevent firing unless activated.

In one aspect, the portable chiropractic adjusting instrument for applying an adjustment energy impulse to a patient is described. In this aspect, the portable chiropractic adjusting instrument can comprise housing, a power source, a thrust tip subassembly, at least one bias element, and a solenoid subassembly. In one aspect, it is contemplated that the housing can define an interior cavity and a port. In another aspect, the power source can be a battery. Optionally, the battery can be a conventional rechargeable battery.

In one aspect, the thrust tip subassembly is mounted in the housing and can comprise a thrust tip plunger having a tip and a base plate that is coupled to and extends substantially transverse to an elongate rod that is configured to be slideably received within the housing. In this aspect, the thrust tip plunger can be configured to be axially movably relative to the housing about and between an extended position and a preload compressed position. Optionally, the thrust tip plunger can be configured to be axially movably relative to the thrust tip mount along the longitudinal axis of the thrust tip mount. In a further aspect, the at least one bias element can be configured to urge the thrust tip plunger in an actuation direction.

In a further aspect, the thrust tip subassembly can also comprise a thrust tip mount having a first end and a spaced second end and defining a core extending an elongate longitudinal axis of the thrust tip mount. In one aspect, the thrust tip mount can be positioned in the housing such that the second end of the thrust tip mount extends to the port. In another aspect, the rod of the thrust tip subassembly can be configured to be slideably received within a portion of the core of the thrust tip mount that is sized to a first internal diameter. Further, the external surface of the tip of the thrust tip subassembly can be configured to be slideably received therein a portion of the core of the thrust tip mount that is sized to a second internal diameter that is greater than the first internal diameter.

In another aspect, the solenoid subassembly can be selectively coupled to the power source and the thrust tip subassembly. In this aspect, it is contemplated that the solenoid subassembly can comprise a solenoid, a solenoid rod and a hammer element. In one aspect, the solenoid defines a core and the solenoid rod can be selectively and conventionally biaxially movable therein the core along a longitudinal axis of the solenoid, which can be co-axial with the longitudinal axis of the thrust tip mount. In this aspect, it is contemplated the solenoid rod is biaxially movable in response to selective application and/or energization by a current supplied by the power source. In one aspect, the hammer element can be coupled to the solenoid rod and spaced from the base plate of the thrust tip plunger at or between a maximal distance when the thrust tip plunger is in the extended position and the solenoid in not activated and a minimal distance when the thrust tip plunger is in the extended position and the solenoid in not activated. In this aspect, the hammer element selectively forcefully contacts the thrust tip plunger in response to selective energization of the solenoid by the current supplied by the power source upon actuation.

In another aspect, the portable chiropractic adjusting instrument can further comprise a preload/safety switch that can be configured to releasably hold the thrust tip plunger of the thrust tip assembly in the preload compressed position. In this aspect, in the preload compressed position, the base plate of the thrust tip plunger is spaced from the hammer element of the solenoid subassembly.

In another aspect, the portable chiropractic adjusting instrument can further comprise an indicator. In a further aspect, the portable chiropractic adjusting instrument can further comprise means for changing the frequency or amplitude of the energy impulse applied to the patient and/or means for measuring the output of the device for a predetermined period of time. In one aspect, the means for measuring the output can comprise at least one transducer configured to measure force and acceleration of the thrust tip plunger.

Further, it is contemplated that in operation, a portable chiropractic adjusting instrument as described and embodied above can be provided to the operator. Subsequently, by sequentially applying the tip of the thrust tip plunger to a desired location and orientation on the patient and actuating the portable chiropractic adjusting instrument, a desired an adjustment energy impulse can be administered to the patient.

EXAMPLE

Four different mechanical shockwave devices were tested to determine the ability of the mechanical shockwave devices to achieve a desired thrust profile. Two of the mechanical shockwave devices were manually operated and exemplified the known spring loaded hammer type mechanical shockwave devices (the Activator II & Activator IV/FS, from Activator Methods International Ltd., Phoenix, Ariz.), while the other two mechanical shockwave devices were electrically powered via an electromagnetic solenoid (the Impulse from Neuromechanical International Ltd., Chandler, Ariz.), and the mechanical shockwave devices of the present invention (hereinafter referred to as the Activator V-E device from Activator Methods LLC, Phoenix, Ariz.).

All devices were tested in a standardized fashion: one component of the device housing was affixed to the testing frame through a machined screw-on collar. The collar prevented a relative motion of the device with respect to the test frame. The rubber cap of the mechanical shockwave devices was removed and an impedance head attached was coupled in replacement. The rubber cap was then replaced on the front of the impedance head. The impedance head included a dynamic load cell and a tri-axial accelerometer.

In front of the device were homogeneous polymer blocks (tissue analogs) and a second dynamic load cell. The polymer blocks were affixed to the load cell, which was rigidly mounted to the frame. The polymer blocks represented ranges of human tissue compliance values that might be seen in the clinic plus additional extreme cases. During device application, the mechanical shock wave propagated from the release mechanism through the impedance head, the rubber cap, and the polymer blocks to the front plate of the resting dynamic load cell. The most compliant component within that line of action was the rubber cap, which was the commercial rubber cap used in the Activator II, IV/FS and V-E devices.

The Activator IV/FS, Activator V-E and the Impulse device were pre-loaded based on the manufacturer's recommendation. For the Activator II device, a pre-set gap distance between the device tip and the tissue analog was determined for each thrust magnitude setting and the device locked in that position.

After pre-loading, the Activator IV/FS and the Activator V-E devices were set to one of their four thrust settings. The four possible settings were selected in random fashion in order to eliminate systematic errors. The same procedure was repeated for the three possible settings of the Impulse device. For the Activator II device, a fraction of the full scale range was selected to represent intermediate values.

| Device | Device Settings | Adjustment Ability |
|---|---|---|
| Activator II (Device #1) | Low (2 revolutions)<br>Medium (4 revolutions)<br>Maximum (7.5 revolutions) | Turning a Knurled Nut |
| Activator IV/FS (Device #2) | 1<br>2<br>3<br>4 | Internal Device Twisting Mechanism |
| Activator V-E (Device #3, Present Invention) | 1<br>2<br>3<br>4 | Thrust Selector Push Button, Electronic Switch |
| Impulse (Device #4) | 1—Low<br>2—Medium<br>3—High | Electronic Toggle Switch |

As the treatment effectiveness depends significantly on the mechanical shockwave to propagate into the body, it is desirable for the shockwave to come as close to a half-sine wave as possible. Vibration damping can be minimized if the shockwave is a pure half-sine wave at or near the eigenfrequency. The shockwave profile is characterized in terms of its crest factor and shape approximation of a half-sine wave, with the deviation expressed in percent. Several additional parameters were extracted and calculated from the recorded thrust output profiles of the four difference devices. Mainly, the peak thrust force in Newtons, the peak thrust acceleration in Meter/Seconds$^2$, the thrust duration or pulse width in Milliseconds, the plunger displacement in Millimeters. The data were tabulated and the mean and standard deviation calculated for each series (N=10). This process was repeated for each device and setting.

Due to the similar profiles of the four mechanical shockwave device types, a fixed-effects statistical model comparison was performed. Major focus was placed on statistical comparison of the peak output force [Newton], the force pulse duration [Milliseconds], the plunger displacement during thrust execution [Millimeter] and the thrust velocity (Meter/Second). Since the similar power settings were utilized for all devices, a multi-factorial analysis of variance (ANOVA) for device type, pulse width, plunger travel and thrust velocity was performed on the mean values of those parameters for all devices. Paired two-tailed T-tests were conducted on the main effects and interactions between devices and parameters.

Figure 16A:
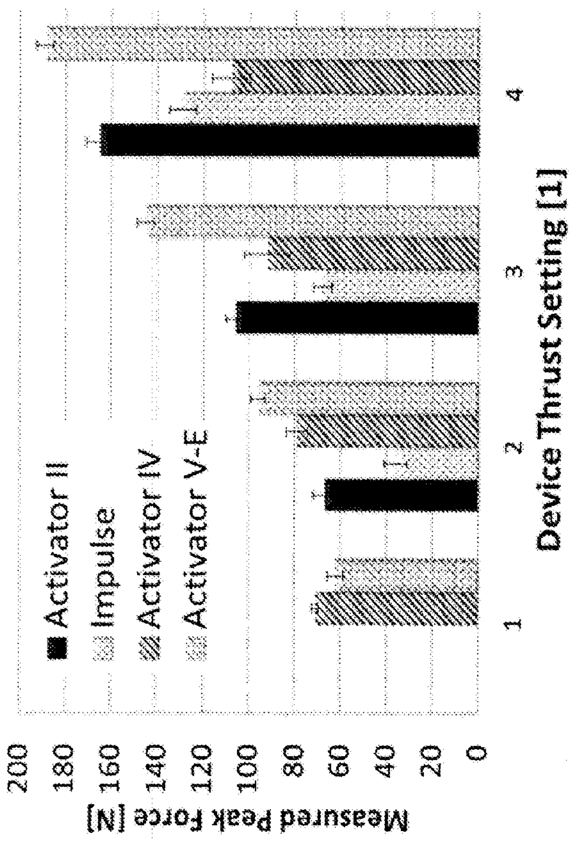
FIGS. 16A and 16B are graphical illustrations showing maximum thrust peak force for the four different mechanical shockwave devices against a stiff tissue analog and a soft tissue analog.
Figure 16B:
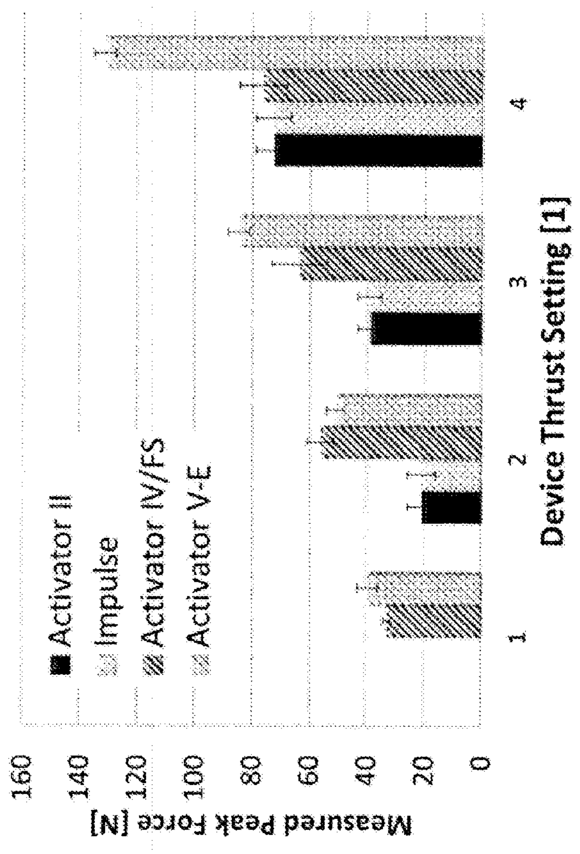

As shown in FIGS. 16A and 16B, all four tested mechanical shockwave devices were substantially equivalent in their thrust force output. Due to its four different settings, the Activator V-E was able to span the largest variable range of thrust values. The device with the least range was the Activator IV/FS. Although the Activator II has an infinite number of adjustment capabilities between its maximum thrust and zero, only three settings were evaluated. The Impulse device achieved a range of thrust values between the Activator IV/FS and the Activator V-E devices. The overall thrust force comparison is depicted for all of the mechanical shockwave devices tested against the 258.07 N/mm polymer block.

The shockwave profile differed significantly between the four tested mechanical shockwave devices and power settings. In general, the pulse width increased with increased compliance of the material and higher power settings. For most devices, the pulse width was between 3 and 7 milliseconds. The exception was the Activator II, which had a pulse width of around 12 milliseconds. Considering this pulse width as part of a half-sine wave, the driving frequency of the Activator II device was around 42 Hz while for the remaining devices had a driving frequency between about 72 to about 150 Hz.

| | Setting 1 | Setting 2 | Setting 3 | Setting 4 |
|---|---|---|---|---|
| Activator V-E | | | | |
| Pulse Width [msec] | 4.70 | 5.79 | 5.15 | 6.88 |
| Peak Force [N] | 62 | 96 | 145 | 189 |
| Velocity [m/sec] | 0.76 | 0.83 | 0.97 | 1.09 |
| Plunger Travel [mm] | 0.82 | 0.89 | 0.97 | 1.10 |
| Activator IV/FS | | | | |
| Pulse Width [msec] | 3.33 | 6.58 | 5.74 | 5.86 |
| Peak Force [N] | 71 | 79 | 92 | 108 |
| Velocity [m/sec] | 0.44 | 1.04 | 0.59 | 0.82 |
| Plunger Travel [mm] | 0.20 | 1.96 | 0.46 | 0.67 |
| Activator II | | | | |
| Pulse Width [msec] | 11.4 | 11.6 | 11.7 | |
| Peak Force [N] | 67 | 106 | 165 | |
| Velocity [m/sec] | 1.07 | 1.82 | 1.35 | |
| Plunger Travel [mm] | 1.99 | 2.96 | 3.19 | |
| Impulse | | | | |
| Pulse Width [msec] | 4.02 | 3.81 | 4.08 | |
| Peak Force [N] | 36 | 68 | 129 | |
| Velocity [m/sec] | 0.63 | 1.02 | 1.22 | |
| Plunger Travel [mm] | 0.93 | 1.0 | 1.24 | |

Figure 15:
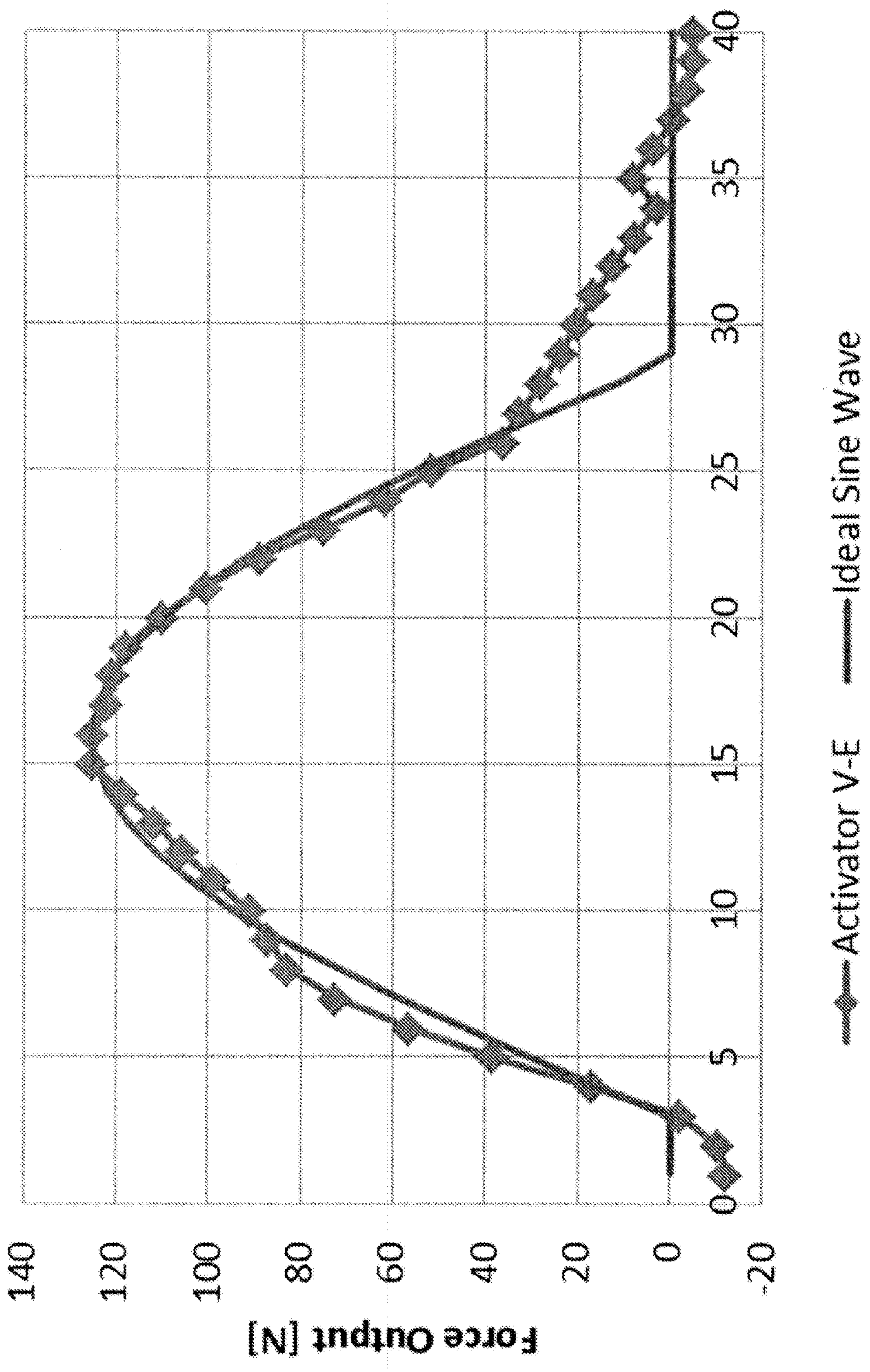
FIG. 15 is a graphical illustration showing a representative shockwave force profile of the generated by the chiropractic adjusting instrument of FIG. 1 (the Activator V-E device) compared to an ideal half-sine wave spanning the same pulse width. As analyzed, the profile matched 96.41% that of the half-sine wave.

The approximation of a half-sine wave with the thrust curves was less achieved with the spring-loaded devices (Activator II and IV/FS mechanical shockwave devices) compared to the more programmable electromagnetically powered devices (Activator V-E and Impulse). On average, the Activator II device captures 48% (±6.1%) of the half-sine wave profile, the Activator IV/FS 74% (±8.3%), the Impulse 83% (±3.9%) and the Activator V-E 94% (±3.5%). This finding is also reflected in the Crest factor, which was 1.13±0.21 for the Activator II device, 1.28±0.16 for the Impulse device, 1.32±0.18 for the Activator IV/FS device, and 1.43±0.16 for the Activator V-E device. One skilled in the art will appreciate that a Crest factor of 1.4142 indicates a perfect half-sine wave. Referring to FIG. 15, in one exemplary test, the shock-wave force profile of the Activator V-E (the portable chiropractic adjusting instrument described herein) matched to within 96.41% of the ideal half-sine wave.

Figure 17:
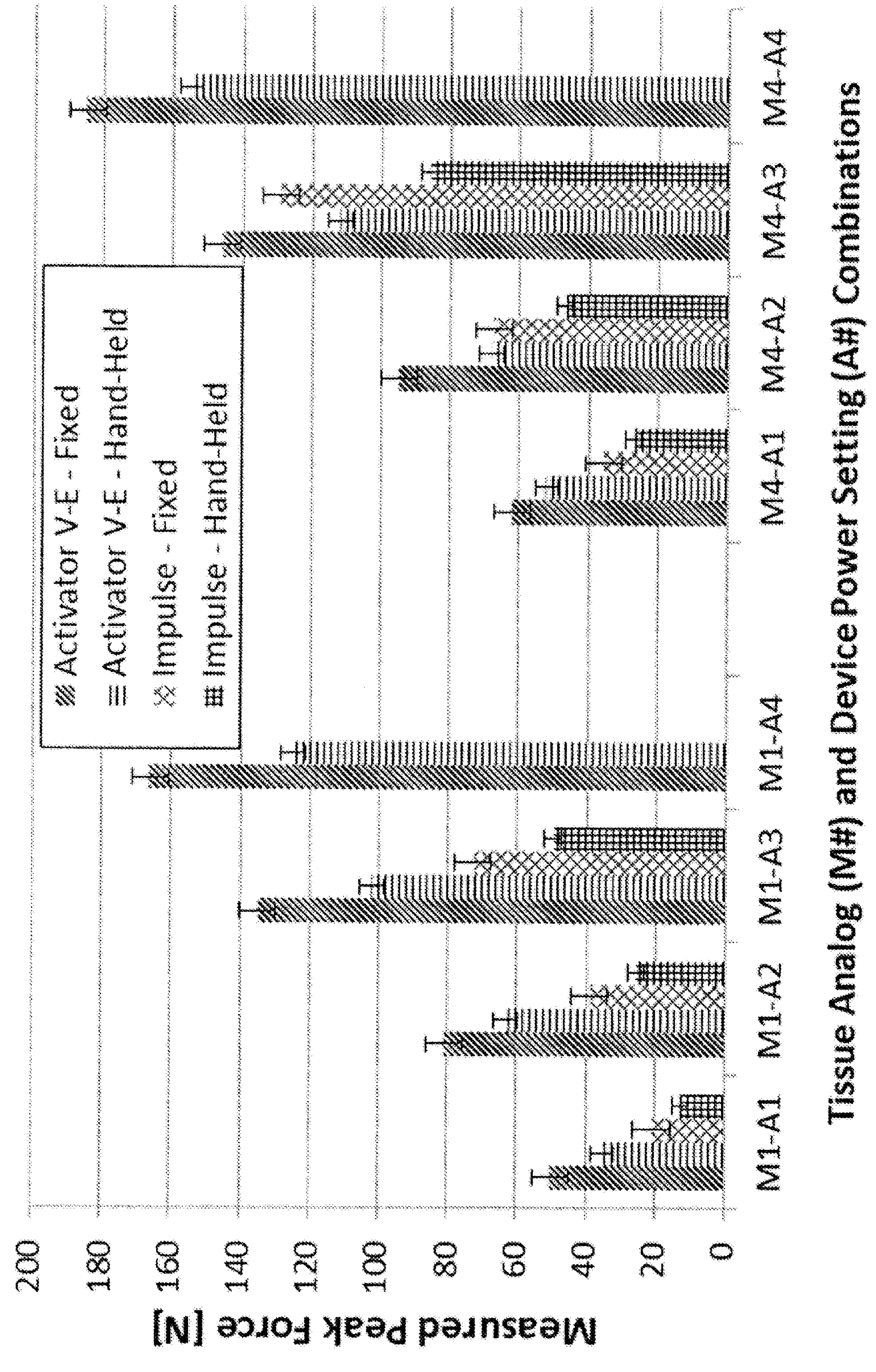
FIG. 17 is a graphical illustration showing peak output force of the Activator V-E and the Impulse device when measured in hand-held operation and fixed frame operation against a stiff tissue analog and a soft tissue analog.
Figure 18:
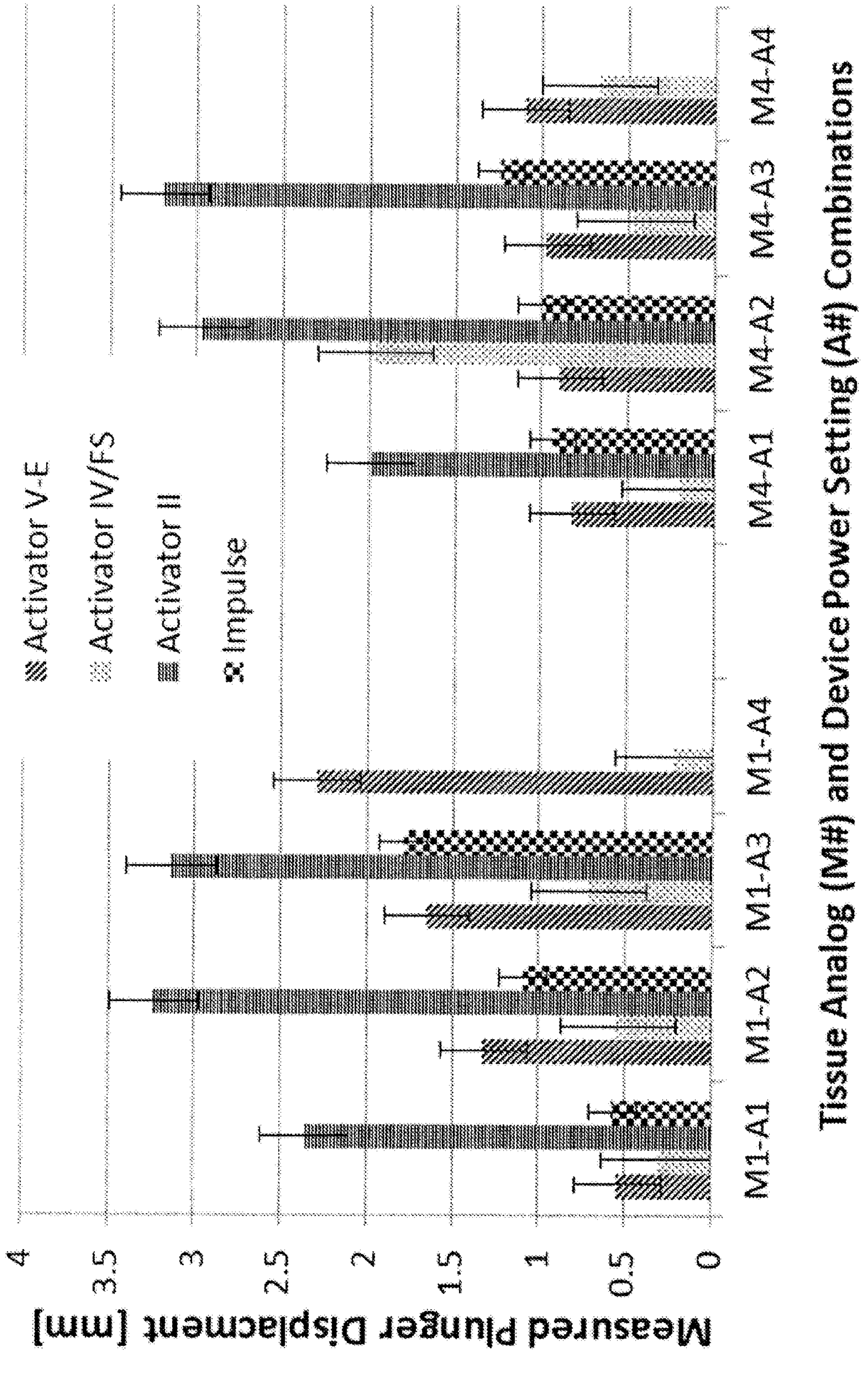
FIG. 18 is a graphical illustration showing plunger displacement for the four different mechanical shockwave devices against a stiff tissue analog and a soft tissue analog.

Similarly to pulse duration, the measured thrust velocity (maximum velocity of the plunger during the force generation phase) is less dependent on the compliance of the tissue analog than on the device power setting. As shown in FIG. 17, the more compliant tissue analog required a larger deformation to generate the measured output force compared to the stiffer tissue analog. Since the pulse width is reasonably constant, a higher velocity is needed to deform a softer material compared to a stiffer one. Referring to FIG. 18, plunger displacement varied proportional with power settings for the stiff material but less so for the softer material. The exception was the Activator II device, which showed a strong correlation between power setting and plunger travel for both tissue analogs.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

What is claimed is:

1. A portable chiropractic adjusting instrument for applying an adjustment energy impulse to a patient, the portable chiropractic adjusting instrument comprising:

- a housing defining an interior cavity and a port; a power source;
- a thrust tip subassembly mounted in the housing comprising:
  - a thrust tip plunger having an elongate rod that is configured to be slideably received within the housing, wherein the thrust tip plunger in configured to be axially movably relative to the housing about and between an extended position and a preload compressed position;
- a solenoid subassembly selectively coupled to the power source and the thrust tip subassembly and comprising:
  - a solenoid that defines a core;
  - a solenoid rod that is selectively movable therein the core along a longitudinal axis of the solenoid in response to selective energization by a current supplied by the power source; and
  - a hammer element coupled to the solenoid rod and spaced from a base plate of the thrust tip plunger at or between a maximal distance when the thrust tip plunger is in the extended position and the solenoid in not activated and a minimal distance when the thrust tip plunger is in the preload compressed position and the solenoid in not activated; and wherein the hammer element selectively forcefully contacts the thrust tip plunger in response to selective energization of the solenoid by the current supplied by the power source upon actuation.

2. The portable chiropractic adjusting instrument of claim 1, wherein the thrust tip subassembly further comprises a thrust tip mount hating a first end and a spaced second end and defining a core extending an elongate longitudinal axis of the thrust tip mount.

3. The portable chiropractic adjusting instrument of claim 2, wherein the thrust tip mount is positioned in the housing such that the second end of the thrust tip mount extends to the port.

4. The portable chiropractic adjusting instrument of claim 2, wherein the thrust tip plunger is configured to be axially movably relative to the thrust tip mount along the longitudinal axis of the thrust tip mount.

5. The portable chiropractic adjusting instrument Of claim 2, wherein the thrust tip plunger has a tip.

6. The portable chiropractic adjusting instrument of claim 5, wherein the rod of the thrust tip plunger is configured to be slideably received within a portion of the core of the thrust tip mount that is sized to a first internal diameter, and wherein the external surface of the tip of the thrust tip plunger is configured to be slideably received therein a portion of the core of the thrust tip mount that is sized to a second internal diameter that is greater than the first internal diameter.

7. The portable chiropractic adjusting instrument of claim 6, wherein the rod of the thrust tip plunger is configured to be slideably received within a portion of the core of the thrust tip mount that is sized to a first internal diameter.

8. The portable chiropractic adjusting instrument of claim 7, wherein the external surface of the tip of the thrust tip plunger is configured to be slideably received therein the portion of the core of the thrust tip mount that is sized to a second internal diameter that is greater than the first internal diameter.

9. The portable chiropractic adjusting instrument of claim 2, wherein the base plate is coupled to and extends substantially transverse to the elongate rod.

10. The portable chiropractic adjusting instrument of claim 9, wherein the longitudinal axis of the solenoid is co-axial with the longitudinal axis of the thrust tip mount.

11. The portable chiropractic adjusting instrument of claim 6, wherein the hammer element is mounted to the distal end of the solenoid rod.

12. The portable chiropractic adjusting instrument of claim 11, wherein the hammer element selectively forcefully contacts the base plate of the thrust tip plunger in response to selective energization of the solenoid by the current supplied by the power source upon actuation.

13. The portable chiropractic adjusting instrument of claim 1, wherein the power source is a battery.

14. The portable Chiropractic adjusting instrument of claim 13, wherein the battery is rechargeable.

15. The portable chiropractic adjusting instrument of claim 1, further comprising a preload/safety switch configured to releasably hold the thrust tip plunger of the thrust tip assembly in the preload compressed position.

16. The portable chiropractic adjusting instrument of claim 1, wherein, in the preload compressed position, the base plate of the thrust tip plunger is spaced from the hammer element of the solenoid subassembly at a predetermined distance.

17. The portable chiropractic adjusting instrument of claim 1, further comprising an indicator.

18. The portable chiropractic adjusting instrument of claim 1, further comprising means for changing the frequency or amplitude of the energy impulse applied to the patient.

19. The portable chiropractic adjusting instrument of claim 1, further comprising means for measuring the output of the device for a predetermined period of time.

20. The portable chiropractic adjusting instrument of claim 19, wherein the means for measuring the output comprises at least one transducer configured to measure force and acceleration of the thrust tip plunger.

21. The portable chiropractic adjusting instrument of claim 1, further comprising at least one bias element configured to urge the thrust tip plunger in an actuation direction.

22. A portable chiropractic adjusting instrument for applying an adjustment energy impulse to a patient, the portable chiropractic adjusting instrument comprising:

a housing defining an interior cavity and a port;

a power source;

a thrust tip subassembly mounted in the housing comprising:

a thrust tip mount having a first end and a spaced second end and defining a core extending an elongate longitudinal axis of the thrust tip mount, wherein the thrust tip mount is positioned in the housing such that the second end of the thrust tip mount extends to the port; and a thrust tip plunger having a tip and a base plate coupled to and extending substantially transverse to an elongate rod, wherein the rod of the thrust tip plunger is configured to be slideably received within the portion of the core of the thrust tip mount that is sized to a first internal diameter, wherein the external surface of the tip of the thrust tip plunger is configured to be slideably received therein the portion of the core of the thrust tip mount that is sized to a second internal diameter that is greater than the first internal diameter, wherein the thrust tip plunger in configured to be axially movably relative to the thrust tip mount along the longitudinal axis of the thrust tip mount about and between an extended position and a preload compressed position;

a solenoid subassembly selectively coupled to the power source and the thrust tip subassembly and comprising:

a solenoid that defines a core;

a solenoid rod that is selectively movable therein the core along a longitudinal axis of the solenoid in response to selective energization by a current supplied by the power source; and a hammer element mounted to the distal end of the solenoid rod, wherein the hammer element is spaced from the base plate of the thrust tip plunger at or between a maximal distance when the thrust tip plunger is in the extended position and the solenoid in not activated and a minimal distance when the thrust tip plunger is in the preload compressed position and the solenoid in not activated; and wherein the hammer element selectively forcefully contacts the base plate of the thrust hp plunger in response to selective energization of the solenoid by the current supplied by the power source upon actuation.

23. The portable chiropractic adjusting instrument of claim 22, wherein the power source is a battery.

24. The portable chiropractic adjusting instrument of claim 23, wherein the battery is rechargeable.

25. The portable chiropractic adjusting instrument of claim 22, further comprising a preload/safety switch configured to releasably hold the thrust tip plunger of the thrust tip assembly in the preload compressed position.

26. The portable chiropractic adjusting instrument of claim 22, wherein, in the preload compressed position, the base plate of the thrust tip plunger is spaced from the hammer element of the solenoid subassembly at a predetermined distance.

27. The portable chiropractic adjusting instrument of claim 22, further comprising an indicator.

28. The portable chiropractic adjusting instrument of claim 22, further comprising a level selector switch for changing the frequency or amplitude of the energy impulse applied to the patient.

29. The portable chiropractic adjusting instrument of claim 22, further comprising means for measuring the output of the device for a predetermined period of time.

30. The portable chiropractic adjusting instrument of claim 29, wherein the means for measuring the output comprises at least one transducer configured to measure force and acceleration of the thrust tip plunger.

31. The portable chiropractic adjusting instrument of claim 22, further comprising at least one bias element configured to urge the thrust tip plunger in an actuation direction and wherein the longitudinal axis of the solenoid is co-axial with the longitudinal axis of the thrust tip mount.

32. A method for applying an adjustment energy impulse to a patient, comprising:

providing the portable chiropractic adjusting Instrument of claim 1 applying the tip of the thrust tip plunger to a desired location and orientation on the patient;

actuating the portable Chiropractic adjusting instrument.

33. A method for applying an adjustment energy impulse to a patient, comprising:

selectively axially moving a thrust tip plunger about and between an extended position and a preload compressed position; and selectively energizing a solenoid to move a hammer element mounted to a distal end of a solenoid rod, wherein the solenoid rod is axially movable along a longitudinal axis in response to selective energization of a solenoid;

wherein the hammer element is spaced from a base plate of the thrust tip plunger at or between a maximal distance when the thrust tip plunger is in the extended position and the solenoid in not activated and a minimal distance when the thrust tip plunger is in the preload compressed position and the solenoid in not activated; and wherein the hammer element selectively forcefully contacts the base plate of the thrust tip plunger in response to selective energization of the solenoid upon actuation.

* * * * *